United States Patent
Sadakane et al.

(10) Patent No.: US 9,526,677 B2
(45) Date of Patent: Dec. 27, 2016

(54) DENTAL CURING COMPOSITION

(71) Applicant: KABUSHIKI KAISHA SHOFU, Kyoto (JP)

(72) Inventors: Yuji Sadakane, Kyoto (JP); Hideto Kasaba, Kyoto (JP); Shunsuke Miyata, Kyoto (JP); Katsuya Kimoto, Kyoto (JP); Toshiyuki Nakatsuka, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 0 days.

(21) Appl. No.: 14/810,792

(22) Filed: Jul. 28, 2015

(65) Prior Publication Data

US 2016/0030299 A1 Feb. 4, 2016

(30) Foreign Application Priority Data

Aug. 1, 2014 (JP) ................................ 2014-158167

(51) Int. Cl.
*A61K 6/083* (2006.01)
*A61K 6/00* (2006.01)

(52) U.S. Cl.
CPC ............. *A61K 6/083* (2013.01); *A61K 6/0073* (2013.01); *A61K 6/0091* (2013.01)

(58) Field of Classification Search
CPC ..... A61K 6/083; A61K 6/0091; A61K 6/0023
USPC ....................................... 523/116; 433/228.1
See application file for complete search history.

(56) References Cited

U.S. PATENT DOCUMENTS

| | | | |
|---|---|---|---|
| 4,362,842 A | 12/1982 | Masuhara et al. | |
| 5,356,951 A | 10/1994 | Yearn et al. | |
| 5,530,038 A | 6/1996 | Yamamoto et al. | |
| 2004/0039080 A1* | 2/2004 | Honda ................... | A61K 6/083 523/120 |
| 2004/0138330 A1 | 7/2004 | Grundler et al. | |

FOREIGN PATENT DOCUMENTS

| | | |
|---|---|---|
| GB | 2 263 115 | 7/1993 |
| JP | 7-91170 | 10/1995 |
| JP | 3276388 | 2/2002 |
| JP | 2011-98941 | 5/2011 |

OTHER PUBLICATIONS

Extended European Search Report issued Jan. 4, 2016 in corresponding European Application No. 15178772.8.

* cited by examiner

*Primary Examiner* — Tae H Yoon
(74) *Attorney, Agent, or Firm* — Wenderoth, Lind & Ponack, L.L.P.

(57) ABSTRACT

The present invention relates to a dental curing composition to restore a lost portion of a tooth generated due to dental caries, tooth fracturing, etc. The dental curing composition has packability suitable for restoring a posterior tooth; has a paste character of avoiding stickiness to a filling instrument; has excellent shaping properties; has very little paste character over time; and has a low polymerization shrinkage property. The dental curing composition comprises: (a) a matrix resin whose viscosity at 25° C. is 10,000 to 17,000 mPa·s, (b) an organic-inorganic composite filler, (c) an inorganic filler, and (d) a polymeric initiator.

3 Claims, No Drawings

DENTAL CURING COMPOSITION

TECHNICAL FIELD

The present invention relates to a dental curing composition to restore a lost portion of a tooth caused by dental caries, tooth fracturing, etc. More particularly, the present invention relates to a dental curing composition that has the paste character suitable for restoring a posterior tooth, that is excellent in the form shaping property, that has the preservation stability for its paste character, and that also has a low polymerization shrinkage property.

BACKGROUND ART

In the dental clinical field, a dental curing composition also called dental filling composite resin is used to esthetically and functionally restore a lost portion of a tooth caused by dental caries, tooth fracturing, etc. The dental curing composition is generally prepared by mixing a matrix resin including several types of polymerizable monomers, various filling materials such as an inorganic filler, an organic-inorganic composite filler, etc., and a polymerization catalyst with each other into a paste form.

Requirements demanded to a dental curing composition can be an excellent handling property for a dentist to execute a filling operation in addition to a high mechanical property, and a color tone and light permeability similar to those of a natural tooth. Describing the handling property in detail, it is preferable that a paste does not stick to a filling instrument when the dental curing composition is injected to fill a cavity or when shaping is executed to restore a tooth form. Further, a character as a stretchy paste tends to be preferred for restoring an anterior tooth while a character as a properly packable paste tends to be preferred for restoring a posterior tooth. The dental curing composition shrinks during polymerization curing and a stress is therefore applied to an adhesive interface between the dental curing composition and the tooth substance caused by shrinkage, and a gap is formed. Thereby, a risk arises that a postoperative pain is caused. Especially, for a posterior tooth, the risk is increased because a high bite pressure is applied thereto. Based on this, a low polymerization shrinkage property is also an important requirement demanded to a dental curing composition.

An approach to cause a packable paste character preferred for restoring a posterior tooth to develop can be an approach of filling a matrix resin with inorganic filler having an average particle diameter of about 0.1 to 5 µm at a high ratio. However, a high-ratio filling is difficult because inorganic filler having such a particle diameter has a large surface area. As a result, the content of the inorganic filler is small and the ratio of the matrix resin is high and shrinkage therefore becomes significant during polymerization curing of the dental curing composition.

On the other hand, Japanese Laid-Open Patent publication No. 2011-98941 proposes a technique according to which hardening of the paste character over time is suppressed by impregnating in advance an organic-inorganic composite filler with a polymerizable monomer whose viscosity at 60° C. is equal to or lower than 10 Pa·s. With this technique, however, a problem arises that the production of the organic-inorganic composite filler becomes complicated because an impregnation process for the polymerizable monomer is added.

Organic-inorganic composite filler having an average particle diameter of about several µm to 30 µm is used in addition to inorganic filler, as a filling material blended in the dental curing composition. The organic-inorganic composite filler is produced by mixing and polymerizing an inorganic filler of about several nm to 0.5 µm with a matrix resin and, thereafter, crushing the polymerized mixture. Generally, organic-inorganic composite filler is not blended alone in a dental curing composition but is blended therein together with the above inorganic filler (Japanese Patent publication No. 7-91170 and Japanese Patent No. 3276388). The organic-inorganic composite filler has advantages that the organic-inorganic composite filler can reduce stickiness of the paste and that the organic-inorganic composite filler can fill the matrix resin at a high ratio.

However, the paste character of the dental curing composition including the organic-inorganic composite filler blended therein tends to be hardened over time due to adsorption of the polymerizable monomer in the matrix resin by the organic substance portion of the organic-inorganic composite filler. Especially, when the amount of filled filler is large, this tendency becomes more noticeable. This phenomenon can be suppressed to some extent by softening the paste character in advance by reducing the amount of filled filler. With this countermeasure, however, no packable paste character can be acquired that is excellent in the shaping property suitable for restoring a posterior tooth, and a problem also arises such as that the polymerization shrinkage becomes significant.

SUMMARY OF THE INVENTION

Problem to be Solved by the Invention

The present invention solves the problem involved in the related art, and an object of the present invention is to provide a dental curing composition that has a packability suitable for restoring a posterior tooth, that has a paste character of avoiding stickiness to a filling instrument, that is excellent in a form shaping property, whose paste character varies little overtime, and that has a low polymerization shrinkage property.

Means for Solving Problem

The inventors actively studied the problem to solve the problem to focus on a viscosity of a matrix resin constituting a dental curing composition, and types and contents, etc., of polymerizable monomers contained in the matrix resin, and revealed that these components influenced the organic-inorganic composite filler constituting the dental curing composition and, thereby, the paste character is varied over time. As a result, the inventors found the following matters to make the present invention.

The matrix resin constituting the dental curing composition has polymerizable monomers each having a high viscosity and polymerizable monomers each having a low viscosity mixed therein at specific ratios. The inventors found that the variation of the paste character over time was able to be suppressed even when the amount of filled filler was large by reducing the mixing ratios of the polymerizable monomers each having a low viscosity and increasing the viscosity of the matrix resin itself, of the components.

The inventors furthermore found that affinity of the matrix resin with the organic-inorganic composite filler is improved and a large amount of filled filler is able to be achieved even when the matrix resin having a high viscosity is used, by including at least one type of the several types of polymerizable monomer used in the production of the organic-inorganic composite filler constituting the dental curing composition, in the matrix resin as a component of the matrix resin constituting the dental curing composition.

Based on the above, the inventors were able to acquire a dental curing composition that has a paste character suitable for restoring a posterior tooth, a form'shaping property using the paste character, and a low polymerization shrinkage property as the present invention.

The present invention relates to the dental curing composition that includes:
(a) a matrix resin having 10,000 to 17,000 mPa·s of viscosity at 25° C.,
(b) an organic-inorganic composite filler,
(c) an inorganic filler, and
(d) a polymeric initiator.

Use of the dental curing composition according to the present invention enables the variation of the paste character over time to be suppressed. The reason why the variation of the paste character over time can be suppressed can be considered as follows. It is conceived that the matrix resin according to the present invention has a high viscosity and the adsorption of the organic-inorganic composite filler to the organic substance portion is therefore suppressed.

The matrix resin according to the present invention may further comprise a low viscosity polymerizable monomer having equal to or lower than 100 mPa·s of viscosity at 25° C., and the content of the low viscosity polymerizable monomer is, for example, equal to or larger than 0.01% by weight and equal to or smaller than 10% by weight to 100% by weight of the matrix resin.

It is conceived that the inclusion of the low viscosity polymerizable monomer causes the low viscosity polymerizable monomer to be adsorbed with priority by the organic substance portion of the organic-inorganic composite filler and suppresses the adsorption of the high viscosity matrix resin to the organic substance portion of the organic-inorganic composite filler and the variation of the paste character over time can therefore be synergistically suppressed.

The reason can be considered as follows why the large amount of filled filler can be achieved notwithstanding the fact that the matrix resin having the high viscosity is used in the dental curing composition of the present invention. The matrix resin constituting the dental curing composition of the present invention comprises as its component at least one type of polymerizable monomer used in the stage of producing the organic-inorganic composite filler. It can be considered that the presence of the common polymerizable monomer, particularly, the mutual action of the common polymerizable monomer included in the matrix resin and common polymerizable monomer included in the organic substance portion of the organic-inorganic composite filler enhances the wettability between the two, thereby, the large amount of filled filler can be achieved.

Effect of the Invention

The present invention enables provision of the dental curing composition that has packability suitable for restoring a posterior tooth, that has a paste character of avoiding stickiness to a filling instrument, that is excellent in the form shaping property, whose paste character varies little over time, and that has a low polymerization shrinkage property.

The "packability" defined herein is an expression that describes easiness of filling (or easiness of squeezing) the dental curing composition into a cavity. Excellent "packability" means: that the paste character has proper elastic force, proper fluidity (a shaping property) is maintained, and a property of avoiding sagging down from a side wall of the cavity is retained (its form can be maintained); and the nature that the composition can fill a cavity to the bottom thereof maintaining the properties without generating any gap between the dental curing composition and a tooth even when the composition is squeezed in the cavity from any direction to fill the cavity therewith. For example, when "packability" of the dental curing composition are excellent like those of the present invention, a dentist can fill the cavity with the composition squeezing the composition to the bottom thereof along the shape thereof without generating any gap between the composition and the tooth and, therefore, the composition is excellent in the handling property, and entrance of any bacteria from a gap between the composition and the tooth, and any peeling of the composition from the tooth can also be prevented. Due to the excellence in "packability", when an operator squeezes the composition into the cavity, the composition can fill the cavity by an amount of the squeezed composition, therefore, the operator can feel the sense to fill the cavity with the composition. For example, when "packability" of the dental curing composition is excellent like those of the present invention, the operator can fill the cavity with the composition feeling as if the operator used amalgam.

On the other hand, a composition causing a user to scarcely feel "packability" significantly deforms its figure by the squeezing force applied thereto during its filling, therefore, the composition cannot maintain its form and it is difficult to squeeze this composition along the shape of the cavity to its bottom. This composition may unevenly be present in the cavity. Due to this, it is difficult to fill the cavity with this composition without generating any gap between the composition and the tooth, therefore, the work efficiency is significantly degraded. Furthermore, the operator cannot feel the sense to fill the cavity with the composition.

MODES FOR CARRYING OUT THE INVENTION

The components of the dental curing composition of the present invention may be described below.

<(a) Matrix Resin>

One of the features of the present invention is that the viscosity of the matrix resin at 25° C. is set to be 10,000 to 17,000 mPa·s. Preferably, a dental curing composition according to the present invention comprises the matrix resin having 10,000 to 17,000 mPa·s of viscosity at 25° C., and also comprises a low viscosity polymerizable monomer having equal to or lower than 100 mPa·s of viscosity at 25° C. by an amount equal to or smaller than 10% by weight to 100% by weight of the matrix resin.

Thereby, adsorption of the matrix resin to the organic substance portion of an organic-inorganic composite filler can be suppressed and, as a result, any variation of the paste character over time can be suppressed.

The matrix resin constituting the dental curing composition of the present invention comprises mono-functional and/or a multi-functional polymerizable monomers generally used in a dental curing composition. The polymerizable monomers are not especially limited and any known polymerizable monomers are usable. Examples of generally and advantageously used typical polymerizable monomers can be polymerizable monomers having an acryloyl group and/or a methacryloyl group. In the present invention, both of the polymerizable monomer having an acryloyl group and/or the polymerizable monomer having a methacryloyl group are comprehensively described by "(meth)acryloyl".

Specific examples of the polymerizable monomers are as follows.

(I) Mono-Functional Polymerizable Monomer:
Methyl(meth)acrylate, ethyl(meth)acrylate, butyl(meth)acrylate, hexyl(meth)acrylate, 2-hydroxyethyl(meth)acrylate, glycidyl(meth)acrylate, lauryl(meth)acrylate, cyclohexyl(meth)acrylate, allyl(meth)acrylate, 2-ethoxyethyl(meth)acrylate, methoxypolyethyleneglycol(meth)acrylate, glycerin(meth)acrylate, isopropyl(meth)acrylate, isobutyl(meth)acrylate, 2-ethylhexyl(meth)acrylate, tetrahydrofurfuryl(meth)acrylate, benzil(meth)acrylate, isobornyl(meth)acrylate, etc.

(II) Aromatic Bifunctional Polymerizable Monomer:
2,2-bis(4-(meth)acryloyloxyphenyl)propane, 2,2-bis(4-(3-(meth)acryloyloxy-2-hidroxypropoxy)phenyl)propane, 2,2-bis(4-(meth)acryloyloxyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2(4-(meth)acryloyloxyethoxyphenyl)-2(4-(meth)acryloyloxydiethoxyphenyl)propane, 2(4-(meth)acryloyloxydiethoxyphenyl)-2(4-(meth)acryloyloxytriethoxyphenyl)propane, 2(4-(meth)acryloyloxydipropoxyphenyl)-2(4-(meth)acryloyloxytriethoxyphenyl)propane, 2,2-bis(4-(meth)acryloyloxydipropoxyphenyl)propane, 2,2-bis(4-(meth)acryloyloxyisopropoxyphenyl)propane, 2,2-bis(4-(meth)acryloyloxypolyethoxyphenyl)propane, etc.

(III) Aliphatic Bifunctional Polymerizable Monomer:
Ethyleneglycoldi(meth)acrylate, diethyleneglycoldi(meth)acrylate, triethyleneglycoldi(meth)acrylate, butyleneglycoldi(meth)acrylate, polyethyleneglycoldi(meth)acrylate, neopentylglycoldi(meth)acrylate, propyleneglycoldi(meth)acrylate, tricyclodecanedi(meth)acrylate, 1,3-butanedioldi(meth)acrylate, 1,4-butanedioldi(meth)acrylate, glycerindi(meth)acrylate, 1,6-hexanedioldi(meth)acrylate, 1,9-nonanedioldi(meth)acrylate, 2-hydroxy-3-acryloyloxypropyldi(meth)acrylate, hydroxy pivalic acid-neopentylglycoldi(meth)acrylate, etc.

(IV) Trifunctional Polymerizable Monomer:
Trimethylolpropanetri(meth)acrylate, trimethylolethanetri(meth)acrylate, trimethylolmethanetri(meth)acrylate, pentaerythritoltri(meth)acrylate, etc.

(V) Tetrafunctional Polymerizable Monomer:
Pentaerythritoltetra(meth)acrylate, ditrimethylolpropanetetra(meth)acrylate, etc.

Specific examples of a urethane-based polymerizable monomer can be di(meth)acrylate, etc., having a bifunctional, or a trifunctional or a higher functional urethane bond and derived from an adduct of a polymerizable monomer having a hydroxyl group such as 2-hydroxyethyl(meth)acrylate, 2-hydroxypropyl(meth)acrylate, or 3-chloro-2-hydroxypropyl(meth)acrylate, and a diisocyanate compound such as methylcyclohexanediisocyanate, methylenebis(4-cyclohexylisocyanate), hexamethylenediisocyanate, trimethylhexamethylenediisocyanate, isophoronediisocyanate, diisocyanatemethylmethylbenzene, or 4,4-diphenylmethanediisocyanate.

In addition to the above polymerizable monomers each including a (meth)acryloyl group, such materials may be used as a polymerizable monomer having an acidic group such as a phosphate group, a phosphonate group, a carboxylic acid group, or a sulfonate group, a polymerizable monomer having a sulfur atom in its molecule, a polymerizable monomer having a fluoro group, a (meth)acrylamide derivative, or an oligomer or a polymer having at least one or more polymerizable group(s).

The matrix resin constituting the dental curing composition of the present invention is prepared by mixing one, or a plurality as necessary of these polymerizable monomers.

The matrix resin constituting the dental curing composition of the present invention includes the polymerizable monomer having a viscosity equal to or lower than 100 mPa·s at 25° C., that is, the low viscosity polymerizable monomer whose content is set to be equal to or smaller than 10% by weight to 100% by weight of the matrix resin. Preferably, the content of the low viscosity polymerizable monomer is equal to or larger than 0.01% by weight and equal to or smaller than 10% by weight to 100% by weight of the matrix resin and, more preferably, is equal to or larger than 0.1% by weight and equal to or smaller than 6% by weight.

The content of the low viscosity polymerizable monomer is set in the above ranges and, thereby, the amount of low viscosity polymerizable monomer can be reduced that is adsorbed by the organic substance portion of the organic-inorganic composite filler and, as a result, hardening of the paste character of the dental curing composition over time can be prevented.

Preferably, the low viscosity polymerizable monomer has a viscosity equal to or lower than 10 mPa·s at 25° C.

Specific examples of the low viscosity polymerizable monomer can be methyl(meth)acrylate, ethyl(meth)acrylate, butyl(meth)acrylate, hexyl(meth)acrylate, 2-hydroxyethyl(meth)acrylate, glycidyl(meth)acrylate, isopropyl(meth)acrylate, isobutyl(meth)acrylate, 2-ethylhexyl(meth)acrylate, methoxypolyethyleneglycol(meth)acrylate, tetrahydrofurfuryl(meth)acrylate, benzil(meth)acrylate, isobornyl(meth)acrylate, ethyleneglycoldi(meth)acrylate, diethyleneglycoldi(meth)acrylate, triethyleneglycoldi(meth)acrylate, butyleneglycoldi(meth)acrylate, polyethyleneglycoldi(meth)acrylate, neopentylglycoldi(meth)acrylate, tricyclodecanedi(meth)acrylate, 1,3-butanedioldi(meth)acrylate, 1,4-butanedioldi(meth)acrylate, glycerindi(meth)acrylate, 1,6-hexanedioldi(meth)acrylate, 1,9-nonanedioldi(meth)acrylate, 2-hydroxy-3-acryloyloxypropyldi(meth)acrylate, trimethylolpropanetri(meth)acrylate, etc.

The matrix resin constituting the dental curing composition of the present invention has a viscosity of 10,000 to 17,000 mPa·s at 25° C. Preferably, the viscosity of the matrix resin may be 10,000 to 15,000 mPa·s at 25° C.

The matrix resin has a viscosity in the above range and, thereby, the amount of polymerizable monomer can be reduced that is adsorbed by the organic substance portion of the organic-inorganic composite filler and, as a result, hardening of the paste character of the dental curing composition over time can be prevented. A sufficient amount of filled filler can be achieved and a paste character can therefore be obtained that has the proper stickiness and that is excellent in the shaping property. The polymerization shrinkage can also be reduced.

The matrix resin constituting the dental curing composition of the present invention may include at least one type of polymerizable monomer used in the stage of producing the organic-inorganic composite filler. Thereby, when the viscosity of the matrix resin is in the range defined by the present invention, affinity between the organic substance portion of the surface of the organic-inorganic composite filler and the matrix resin may be improved and high wettability of the matrix resin with the organic-inorganic composite filler is developed. A large amount of filled filler can therefore be achieved in the dental curing composition.

The content of the matrix resin in the dental curing composition is preferably 10 to 25% by weight, more preferably, 10 to 20% by weight to 100% by weight of the dental curing composition. By setting the content of the matrix resin in the dental curing composition to be in such ranges, a dental curing composition can be produced in a paste form, which has a paste character that presents proper stickiness and that is excellent in packability. The polymerization shrinkage can also be reduced.

<(b) Organic-Inorganic Composite Filler>

The organic-inorganic composite filler constituting the dental curing composition of the present invention is produced by mixing and polymerizing the polymerizable monomers with an inorganic filler and, thereafter, crushing the mixture. Any known polymerizable monomer is usable without any limitation of the mono-functional and/or the multi-functional polymerizable monomers generally used in dental curing compositions as the polymerizable monomer used in the production of the organic-inorganic composite filler, similarly to the polymerizable monomers used in the matrix resin. The inorganic filler used in the production of the organic-inorganic composite filler is not especially limited and any known inorganic filler used in the dental field is usable. The shape of the inorganic filler is an arbitrary particle shape such as a spherical shape, a needle-like shape, a plate-like shape, a fracture shape, a scale shape, or a porous shape, and is not especially limited. The shape may be a shape of an aggregate of those. The type of inorganic filler is also not especially limited.

Specific examples of the inorganic filler can be inorganic oxides and inorganic complex oxides such as silica, alumina, titania, zirconia, strontium oxide, barium oxide, yttrium oxide, lanthanum oxide, ytterbium oxide, silica-zirconia, silica-titania, silica-titania-barium oxide, and silica-titania-zirconia, glasses such as molten silica, quartz, aluminosilicate glass, borosilicate glass, alminoborate glass, and boroaluminosilicate glass, metallic fluorides such as sodium fluoride, calcium fluoride, barium fluoride, strontium fluoride, yttrium fluoride, lanthanum fluoride, and ytterbium fluoride, calcium carbonate, talc, kaolin, clay, mica, aluminum sulfate, calcium sulfate, barium sulfate, calcium phosphate, hydroxyapatite, silicon nitride, aluminum nitride, titanium nitride, silicon carbide, boron carbide, calcium hydroxide, strontium hydroxide, and zeolite.

Each of these inorganic fillers alone or some thereof in combination is/are usable in the production of the organic-inorganic composite filler. Of these, from a viewpoint of adding a high X-ray radiological property to the dental curing composition, preferably, aluminosilicate glass, borosilicate glass, alminoborate glass, or boroaluminosilicate glass including a metal such as strontium, barium, or lanthanum and/or fluorine is used as the inorganic filler included in the organic-inorganic composite filler. Preferably, the average particle diameter of these inorganic fillers is in a range from 0.01 to 10 µm and, more preferably, in a range from 0.01 to 2.0 µm. Especially, from a viewpoint of causing the dental curing composition to have a high polishing property, and surface smoothness and surface gloss after polishing, preferably, inorganic fillers are used whose average primary particle diameter is equal to or smaller than 0.8 µm as the inorganic fillers.

Preferably, each of these inorganic fillers may be made hydrophobic by applying thereto a surface preparation process in advance before being used in the production of the organic-inorganic composite filler. The application of the surface preparation process enables the high ratio filling of the inorganic filler in the organic-inorganic composite filler and the mechanical strength of the organic-inorganic composite filler is therefore improved. The surface preparation agent used in the surface preparation process for the inorganic filler is not especially limited and any known surface preparation agent is usable such as an organosilicon compound, an organozirconium compound, or an organotitanium compound while the most generally used surface preparation agent is the organosilicon compound. Examples of the organosilicon compound can be methyltrimethoxysilane, ethyltrimethoxysilane, methoxytripropylsilane, propyltriethoxysilane, hexyltrimethoxysilane, vinyltrimethoxysilane, vinyltriethoxysilane, vinyltrichlorosilane, vinyltri(β-methoxyethoxy)silane, γ-methacryloyloxypropyltrimethoxysilane, γ-glycidoxypropyltrimethoxysilane, γ-mercaptopropyltrimethoxysilane, γ-aminopropyltrimethoxysilane, 3-aminopropyltriethoxysilane, methyltrichlorosilane, phenyltrichlorosilane, trimethylsilylisocyanate, vinylsilyltriisocyanate, and phenylsilyltriisocyanate. Each of these compounds alone or some thereof in combination is/are usable. The method of the surface preparation process is not especially limited and any known method thereof is applicable.

The production method of the organic-inorganic composite filler is not especially limited and any method thereof can be employed. The polymerizable monomer, the inorganic filler, and the polymeric initiator are first mechanically kneaded using a mortar, a kneader, a roll, a raikai mixer etc., to prepare a paste as a production method of the organic-inorganic composite filler known in the dental field. The polymeric initiator is not especially limited, and any known radical generating agent is usable without any limitation such as a photo polymeric initiator, a chemical polymeric initiator, a thermal polymeric initiator, etc., while the thermal polymeric initiator is most generally used. For example, preferably, an organic peroxide such as benzoyl peroxide, an azo compound such as azobisisobutyronitrile, or an organic metallic compound such as tributylboron is used as the thermal polymeric initiator. Each of these polymeric initiators alone or some thereof in combination is/are usable regardless of the polymerization type and the polymerization method. The amount of polymeric initiator to be added only has to properly be selected from a range from 0.1 to 10% by weight to the polymerizable monomers. Preferably, the content of the inorganic filler included in the organic-inorganic composite filler is in a range from 10 to 85% by weight and, more preferably, in a range from 40 to 85% by weight. Problems arise concerning the mechanical strength, the surface hardness, the thermal expansion coefficient, etc., of the organic-inorganic composite filler when the content is less than the ranges and, on the other hand, problems arise concerning the mechanical strength, the polishing property, etc., caused by degradation of the dispersibility of the inorganic filler in the organic-inorganic composite filler when the content exceeds the ranges.

The paste may be caused to polymerize using proper polymerization equipment such as a hot press. The polymerization temperature only has to properly be selected corresponding to the decomposition temperature of the polymeric initiator while, preferably, the polymerization temperature is in a range from 20 to 250° C. and, more preferably, is in a range from 60 to 200° C. The polymerization time period only has to properly be selected taking into consideration the polymerization state of the polymerized substance and the amount of remaining unreacted monomers. The polymerization can also generally be caused to take place in an inert gas such as nitrogen or argon to prevent any change of the color of the polymerized substance. Polymerization under the atmospheric pressure is sufficient as the polymerization while the polymerization can also be caused to take place under an increased pressure as necessary. The preparation and the polymerization of the paste can also be caused to concurrently take place using a kneader such as a pressurizing kneader.

After the polymerization of the paste, the polymerized substance is crushed to acquire an organic-inorganic composite filler. The crushing method is not especially limited while the crushing can be executed in a method generally employed in the dental field. For example, the method can be a method using a container driven medium mill such as a ball mill or a vibration mill, a high speed rotation mill such as a hammer mill or a turbo mill, or a medium agitation mill such as a sand grinder or an attritor, and can properly be selected corresponding to the necessary average particle diameter. The crushing can also be executed in an atmosphere of an inert gas or a solvent such as alcohol to prevent any coloring of the crushed substance during the crushing. The crushing can also be executed with an antioxidizing agent such as, for example, a known phenol such as hydroquinone monomethyl ether added to the polymerized paste. Preferably, the average particle diameter of the crushed organic-inorganic composite filler is in a range from 1 to 100 µm. More preferably, the average particle diameter thereof is in a range from 3 to 50 µm and, yet more preferably, is in a range from 5 to 30 µm. Preferably, the organic-inorganic composite filler after being crushed is treated with the same surface preparation agent as that used in the surface preparation process of the inorganic filler. Due to the surface preparation process, the organic-inorganic composite filler can fill the matrix resin at a high ratio, and the mechanical strength of the dental curing composition may be therefore improved and the polymerization shrinkage may be reduced. The produced organic-inorganic composite filler is usable alone or a plurality thereof are usable in combination. Preferably, the content of the organic-inorganic composite filler in the dental curing composition is 15 to 80% by weight to 100% by weight of the dental curing composition, more preferably 15 to 50% by weight, yet more preferably 15 to 35% by weight, and especially preferably 20 to 35% by weight. Setting the content of the organic-inorganic composite filler to be in these ranges can prevent any high viscosity of the paste and can reduce the polymerization shrinkage. The dental curing composition can have advantageous mechanical strength as a dental material.

<(c) Inorganic Filler>

The inorganic filler constituting the dental curing composition of the present invention is not especially limited and any known inorganic filler used in the dental field is usable. The shape thereof can be a spherical shape, a needle-like shape, a plate-like shape, a fracture shape, a scale shape, or a porous shape, and is not especially limited. The shape may be a shape of an aggregate of those. The type of inorganic filler is also not especially limited. Specific examples of the inorganic filler are same as those of the inorganic filler used in the production of the organic-inorganic composite filler. The inorganic filler can be used alone or a plurality of those can be used in combination. Preferably, the content of the inorganic filler in the dental curing composition is 10 to 75% by weight to 100% by weight of the dental curing composition and more preferably is 20 to 75% by weight. Setting the content of the inorganic filler in the dental curing composition to be in these ranges enables the dental curing composition to have advantageous mechanical strength and proper stickiness as a dental material and provides a paste character with an excellent shaping property.

<Contents of Organic-Inorganic Composite Filler and Inorganic Filler in Dental Curing Composition>

The dental curing composition of the present invention has the organic-inorganic composite filler and the inorganic filler combined with each other and filled at high ratios therein. Thereby, the dental curing composition tends to avoid stickiness to any filling instrument, is excellent in the shaping property, and can cause its packability paste character and its low polymerization shrinkage property to develop. Preferably, the total content of the organic-inorganic composite filler and the inorganic filler in the dental curing composition is equal to or larger than 75% by weight to 100% by weight of the dental curing composition, and more preferably is equal to or larger than 80% by weight. Setting the total content of the organic-inorganic composite filler and the inorganic filler in the dental curing composition to be in the ranges enable desired stickiness to be obtained, a paste character excellent in the packability to be acquired, and the polymerization shrinkage to be reduced.

Preferably, the ratios of the organic-inorganic composite filler and the inorganic filler in the dental curing composition are the organic-inorganic composite filler:the inorganic filler=1:5 to 8:1 as the ratios by weight.

<(d) Polymeric Initiator>

The polymeric initiator constituting the dental curing composition of the present invention is not especially limited and any known radical generating agent is usable. Polymeric initiators are generally classified roughly into those that each cause polymerization to start by being mixed immediately before the use (chemical polymeric initiators), those that each cause polymerization to start by being heated or warmed (thermal polymeric initiators), and those that each cause polymerization to start by receiving application of a light beam (photo polymeric initiators).

The chemical polymeric initiators can be the series of redox-type polymeric initiators each including an organic peroxide/an amine compound/a sulfinate or an organic peroxide/an amine compound/a borate compound, and the series of organic-metal-type polymeric initiators that each cause polymerization to start by reacting with oxygen or water. Sulfinates and borate compounds can also cause polymerization to start by reacting with a polymerizable monomer including an acidic group.

Specific examples of the organic peroxide can be benzoyl peroxide, parachlorobenzoyl peroxide, 2,4-dichlorobenzoyl peroxide, acetyl peroxide, lauroyl peroxide, tertiary-butyl peroxide, cumenehydro peroxide, 2,5-dihydro peroxide, methylethylketone peroxide, and tertiary-butylperoxybenzoade.

Preferably, specific examples of amine compounds are secondary or tertiary amine formed by an amino group bonded to an aryl group, and specific examples thereof can be p-N,N-dimethyl-toluidine, N,N-dimethylaniline, N-β-hydroxyethyl-aniline, N,N-di(β-hydroxyethyl)-aniline, p-N,N-di(β-hydroxyethyl)-toluidine, N-methyl-aniline, and p-N-methyl-toluidine.

Specific examples of sulfinates can be sodium benzenesulfinate, lithium benzenesulfinate, and sodium p-toluenesulfinate.

Specific examples of the borate compound can be sodium salts, lithium salts, potassium salts, magnesium salts, tetrabutylammonium salts, and tetramethylammonium salts of trialkylphenylboronate and trialkyl(p-phlorophenyl)borate (alkyl groups are an n-butyl group, an n-octyl group, an n-dodecyl group, etc.).

Specific examples of the organic-metal-type polymeric initiator can be organic boron compounds such as triphenylborane, tributylborane, and a partially oxidized tributylborane.

Azo compounds such as azobisisobutyronitrile, azobisisomethylisobutyrate, and azobiscyanovalerate are advantageously used as the thermal polymeric initiators each causing polymerization to start by being heated or warmed, in addition to the organic peroxides.

The photo polymeric initiator can be that including a photo sensitization agent, and a photo sensitization agent/photo polymerization accelerator. Specific examples of the photo sensitization agent can be α-diketones such as benzil, camphorquinone, α-naphthyl, acetonaphthene, p,p'-dimethoxybenzil, p,p'-dichlorobenzilacetyl, petanedione, 1,2-phenanthrenequinone, 1,4-phenanthrenequinone, 3,4-phenanthrenequinone, 9,10-phenanthrenequinone, and naphthoquinone, benzoinalkylethers such as benzoin, benzoinmethylether, and benzoinethylether, thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone, and 2,4-diisopropylthioxanthone, benzophenones such as benzophenone, p-chlorobenzophenone, and p-methoxybenzophenone, acyl-phosphine oxides such as 2,4,6-trimethylbenzoyldiphenyl-phosphine oxide and bis(2,6-dimethoxybenzoyl)-2,4,4-trimethylpentyl-phosphine oxide, α-aminoacetophenones such as 2-benzyl-dimethylamino-1-(4-morpholinophenyl)-butanone-1, and 2-benzyl-diethyl-amino-1-(4-morpholinophenyl)-propanone-1, ketals such as benzyldimethylketal, benzyldiethylketal, and benzyl(2-methoxyethylketal), titanocenes such as bis(cyclopentadienyl)-bis(2,6-difluoro-3-(1-pyrrolyl)phenyl)-titanium, bis(cyclopentadienyl)-bis(pentanefluorophenyl)-titanium, and bis(cyclopentadienyl)-bis(2,3,5,6-tetrafluro-4-disiloxyphenyl)-titanium.

Specific examples of the photo polymerization agent can be tertiary amines such as N,N-dimethylaniline, N,N-diethylaniline, N,N-di-n-butylaniline, N,N-dibenzylaniline, p-N, N-dimethyl-toluidine, m-N,N-dimethyl-toluidine, p-N,N-diethyl-toluidine, p-bromo-N,N-dimethylaniline, m-chloro-N, N-dimethylaniline, p-dimethylaminobenzaldehyde, p-dimethylaminoacetophenone, p-dimethylamino-benzoic acid, p-dimethylamino-benzoic acid-ethylester, p-dimethylamino-benzoic acid-aminoester, N,N-dimethyl-anthranilic acid-methylester, N,N-dihydroxyethylaniline, p-N,N-dihydroxyethyl-toluidine, p-dimethylaminophenylalcohol, p-dimethylaminostyrene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethylmethacrylate, N,N-diethylaminoethylmethacrylate, and 2,2'-(n-butylimino)diethanol, secondary amines such as N-phenylglycine, barbituric acids such as 5-butyl-barbituric acid, and 1-benzyl-5-phenyl-barbituric acid, tin compounds such as dibutyltin-diacetate, dibutyltin-dilaurate, dioctyltin-dilaurate, dioctyltin-didecanoate, dioctyltin-bis(mercaptoacetic acid-isooctylester)salt, and tetramethyl-1,3-diacetoxydistanoxan, aldehyde compounds such as laurylaldehyde and terephthalaldehyde, and sulfur-including compounds such as dodecylmercaptan, 2-mercaptobenzoxazole, 1-decanethiol, and thiosalicylic acid.

To improve the photo polymerization acceleration capacity, addition of such oxycarboxylic acids may be effective in addition to the photo polymerization accelerators, as citric acid, malic acid, tartaric acid, glycolic acid, gluconic acid, α-oxyisobutyric acid, 2-hydroxypropanoic acid, 3-hydroxypropanoic acid, 3-hydroxybutanoic acid, 4-hydroxybutanoic acid, and dimethylolpropionic acid.

Each of these polymeric initiators alone or some thereof in combination is/are usable regardless of the polymerization type and the polymerization method. No problem arises from these polymeric initiators even when a secondary processing is applied to any of the polymeric initiators as necessary such as encapsulation thereof in micro capsules.

A preferred aspect is use of the photo polymeric initiator of these polymeric initiators, that generates radicals when a light beam is applied thereto and that is most advantageously used based on the fact that the photo polymeric initiator can cause the dental curing composition to polymerize when little air is included in the dental curing composition. More preferably, a combination of α-diketone and a tertiary amine of the photo polymeric initiators is used and, most preferably, a combination is used of camphorquinone, and an aromatic amine having therein an amino group such as p-N,N-dimethylaminoethylbenzoate directly bonded to a benzene ring or an aliphatic amine having a double bond in a molecule such as N,N-dimethylaminoethylmethacrylate. In addition, corresponding to the use, such substances can arbitrarily be used as sensitizing dyes based on coumalin, cyanine, thiazine, etc., photo-acid-generating agents that each generate Brønsted acid or Lewis acid when a light beam is applied thereto such as a halomethyl-group-displaced-s-triazine derivative and diphenyliodonium-salt compound, quaternary ammonium halides, and transition metal compounds.

The content of the polymeric initiator constituting the dental curing composition of the present invention can arbitrarily be selected corresponding to the use while, preferably, the content thereof is in a range from 0.1 to 10 parts by weight to 100 parts by weight of the matrix resin and, more preferably, is in a range from 0.1 to 5 parts by weight.

<Other Additives>

In addition to the (a) to (d) components, known additives may be blended in the dental curing composition of the present invention each within a range not to degrade the effect of the present invention. For example, the additives can be fillers (organic fillers) other than (b) the organic-inorganic composite filler and (c) the inorganic filler, polymerization-inhibitor, antioxidizing materials, ultraviolet absorbing materials, antibacterial materials, dyes, and pigments.

The polymerization-inhibitor includes, for example, 2,6-di-butylhydroxytoluene, hydroquinone, dibutylhydroquinone, dibutylhydroquinonemonomethylether, 2,6-tert-butylphenol. The ultraviolet absorbing materials include, for example, 2-(2'-hydroxy-5'-methylphenyl)benzotriazole, and 4-tert-butylphenylsalicylate.

The pigments include, for example, black iron oxide, ferric oxide, yellow iron oxide, and titanium oxide.

The dental curing composition of the present invention may be prepared by mixing the above components. The variation over time of the consistency of the paste of the dental curing composition can be determined using a method described in the item (4) Preservation Stability in Examples. The dental curing composition is usually stored or used at a temperature equal to or lower than 30° C. while, in such a case, the variation of the consistency gradually advances over several months to several years depending on the amount of each blended component. On the other hand, the variation of the consistency can be checked in a relatively short time by conducting an accelerated test by storing the dental curing composition at 50° C. According to the reviews by the inventors, preferably, the maintenance rate of the consistency in the case where the dental curing composition is stored at 50° C. for one month (the consistency after the 50° C.-one month storage/the initial consistency×100) is equal to or higher than 85% and, more preferably, is equal to or higher than 90%. When this condition is satisfied, the dental curing composition may maintain its consistency for a long time under the condition for its ordinary storage or use.

The packaging form of the dental curing composition of the present invention is not especially limited, and any one of a one-pack packaging form, two-pack packaging form, and another form can be used depending on the type of the polymeric initiator or the purpose of use. The packaging form can arbitrarily be selected corresponding to the use.

EXAMPLES

The present invention is described in more detail and specifically with reference to Examples. However, the present invention is not limited to Examples.

The materials used in Examples and Comparative Examples and their abbreviations are listed below.
[Polymerizable Monomer]
  Bis-GMA:
2,2-bis[4-(3-methacryloyloxy-2-hydroxypropoxy)phenyl]propane (the viscosity at 50° C.: 15,000 mPa·s)
  UDA:
1,6-bis[(1-acryloyloxy-3-phenoxy)-2-isopropoxycarbonylamino]hexane (the viscosity at 50° C.: 3,000 mPa·s)
  UDMA:
N,N-(2,2,4-trimethylhexamethylene)bis[2-(aminocarboxy)ethanol]methacrylate (the viscosity at 25° C.: 8,000 mPa·s)
  Bis-MPEPP:
2,2-bis(4-methacryloyloxypolyethoxyphenyl)propane (the viscosity at 25° C.: 1,000 mPa·s)
[Low Viscosity Polymerizable Monomer (Polymerizable Monomer Having Viscosity Equal to or Lower than 100 mPa·s at 25° C.)]
  3G: Triethyleneglycoldimethacrylate (the viscosity at 25° C.: 4 mPa·s)
  NPG: Neopentylglycoldimethacrylate (the viscosity at 25° C.: 2 mPa·s)
  TMPT: Trimethylolpropanetrimethacrylate (the viscosity at 25° C.: 46 mPa·s)
[Inorganic Filler]
  Bariumboroaluminosilicate glass filler (the average particle diameter: 1 μm)
  Fluoroaluminosilicate glass filler 1 (the average particle diameter: 1 μm)
  Fluoroaluminosilicate glass filler 2 (the average particle diameter: 3 μm)
  Aerosil R972 (an ultra fine particle filler)
[Polymerization Accelerator]
  DMABE: N,N-dimethylaminoethylbenzoate
[Polymeric Initiator]
  BPO: Benzoyl peroxide
  CQ: α-camphorquinone
[Surface Preparation Agent]
  γ-MPS: γ-methacryloyloxypropyltrimethoxysilane The testing methods employed for Examples and Comparative Examples are as follows.
(1) Viscosity
65 g of the matrix resin was put in a 50-mL glass bottle, and the bottle was statically stored in a temperature-controlled chamber at 25° C. (the humidity: 50%) for one day. After the static storage for one day, the viscosity of the matrix resin was measured at 25° C. using a Brookfield viscosity meter (manufactured by Toki Sangyo Co., Ltd., Model: BMII). The value acquired three min after the start of the measurement was taken as the viscosity.
(2) Stickiness
The stickiness was evaluated by filling a model of a first-order cavity with the dental curing composition using a filling instrument. The evaluation criteria were as follows.
A: The stickiness was scarcely felt.
B: The stickiness was felt.
(3) Packability (Toughness and the Elasticity)
The packability was evaluated by filling a model of a first-order cavity with the dental curing composition using a filling instrument. The evaluation criteria were as follows. The packability was determined to be excellent for the evaluation criteria of A and B.
A: The packability was sufficiently felt and it was very easy to fill the cavity with the dental curing composition.
B: The packability was felt and it was easy to fill the cavity with the dental curing composition.
C: The packability was somewhat felt and the cavity was able to be filled with the dental curing composition.
D: The packability was scarcely felt and it was difficult to fill the cavity with the dental curing composition.
(4) Preservation Stability
The dental curing composition was statically stored in a temperature-controlled chamber at 25° C. (the humidity: 50%) for one day, and 300 mm$^3$ of the dental curing composition was weighed on a glass plate. Another glass plate was put on the dental curing composition and a weight weighing 385 g was further placed thereon. Thereafter, the dental curing composition was left in this state for three min. After three min, the weight was removed, and the dimensions between parallel cutting lines of the dental curing composition spread in a circle were measured at two points. The average value of the values at the two points was taken as the initial consistency (mm). The dental curing composition was statically stored in a temperature-controlled container at 50° C. (the humidity: 50%) for one month, and, the consistency thereof was measured using the above method concerning the dental curing composition statically stored in the temperature-controlled chamber at 25° C. (the humidity: 50%) for one day. The obtained consistency was taken as the consistency (mm) after the storage at 50° C.

From these obtained values of the consistency, the consistency maintenance rate (%) was calculated according to Eq. (I) and, thereby, the preservation stability of the dental curing composition was evaluated. When the consistency maintenance rate was equal to or higher than 85%, the preservation stability was determined to be excellent.

Consistency maintenance rate (%)=the consistency after the storage at 50° C./the initial consistency×100          (I)

(5) Polymerization Shrinkage Rate
A stainless steel mold (the inner diameter: 10 mm, the thickness: 2 mm) was filled with the dental curing composition and cover glasses were placed on its both side faces to be brought into pressurized contact with the mold. Thereafter, a light beam was applied to the dental curing composition from the side faces each for three min using a visible light irradiator (Solidylite V: manufactured by Shofu Inc.) and, thereby, a cured body of the dental curing composition was obtained. The densities of the dental curing composition before and after light-curing were measured using a gas pycnometer (Acupyc 1303: manufactured by Micromeritics), and the polymerization shrinkage rate was calculated from the acquired measurements according to Eq. (II). The measurement of the densities was conducted at 25° C.

Polymerization Shrinkage Rate $$(\text{vol \%}) = (1 - D_{before}/D_{after}) \times 100 \quad \text{(II)}$$

($D_{before}$: The density of the dental curing composition before light-curing, $D_{after}$: The density of the dental curing composition after light-curing)

(Production of Organic-Inorganic Composite Filler)

According to an ordinary method, a surface preparation of 100 parts by weight of the bariumboroaluminosilicate glass filler (the average particle diameter: 1 µm) was executed with 6 parts by weight of γ-MPS to obtain a barium glass filler.

70 parts by weight of the barium glass fill was mixed with 30 parts by weight of a mixture including 50 parts by weight of Bis-GMA, 50 parts by weight of 3G, and 0.5 parts by weight of BPO, and the final mixture was evenly kneaded. Thereafter, the mixture was cured by heating the mixture at 100° C. for 4 hours in a nitrogen atmosphere, and was crushed and classified. Thereby, powder having the average particle diameter of 25 µm was obtained. According to an ordinary method, a surface preparation of 100 parts by weight of this powder was executed with 6 parts by weight of γ-MPS to obtain the organic-inorganic composite filler.

(Production of Inorganic Filler A)

According to an ordinary method, a surface preparation of 100 parts by weight of the fluoroaluminosilicate glass filler 1 (the average particle diameter: 1 µm) was executed with 8 parts by weight of γ-MPS. Thereby, the inorganic filler "A" was obtained.

(Production of Inorganic Filler B)

According to an ordinary method, a surface preparation of 100 parts by weight of the fluoroaluminosilicate glass filler 2 (the average particle diameter: 3 µm) was executed with 4 parts by weight of γ-MPS. Thereby, the inorganic filler "B" was obtained.

(Inorganic Filler C)

Aerosil R972 (manufactured by Nippon Aerosil Co., Ltd.) was used as the inorganic filler "C".

(Preparation of Matrix Resin and Measurement of Viscosity Thereof)

The matrix resins R-1 to 9 were prepared by mixing each polymerizable monomer at the ratios shown in Table 1. According to the method described in (1) Viscosity, the viscosity of each of the prepared matrix resins was measured. The measurement results thereof are also shown in Table 1 together with the ratios. After the measurement of the viscosities of the matrix resins, 1 part by weight of DMABE and 0.3 parts by weight of CQ were melted in 100 parts by weight of each of the matrix resins. This mixture liquid was used as "the matrix resin including the polymerization catalyst" in the preparation of the dental curing composition.

(Preparation of Dental Curing Composition)

After kneading the components at the ratios shown in Table 2, the kneaded components were defoamed under vacuum. Thereby, dental curing compositions each in a paste form (Examples 1 to 9 and Comparative Examples 1 to 7) were prepared. For the prepared dental curing compositions, the stickiness, the packability, the preservation stability, and the polymerization shrinkage rate were measured according to the above methods. The measurement results are shown in table 2.

TABLE 1

| | Polymerizable Monomer (parts by weight) | | | | | | | | |
|---|---|---|---|---|---|---|---|---|---|
| | | | | | Low Viscosity Polymerizable Monomer | | | | Viscosity |
| Matrix Resin No. | Bis-GMA | UDA | UDMA | Bis-MPEPP | 3G | NPG | TMPT | Total | [mPa · s] |
| R-1 | 40 | — | 30 | 25 | 5 | — | — | 100 | 13,620 |
| R-2 | 40 | — | 20 | 35 | 5 | — | — | | 11,020 |
| R-3 | 40 | — | 10 | 45 | 5 | — | — | | 8,580 |
| R-4 | 40 | 30 | — | 20 | 10 | — | — | | 11,820 |
| R-5 | 40 | 10 | — | 40 | 10 | — | — | | 4,640 |
| R-6 | 40 | 10 | — | 35 | 15 | — | — | | 3,260 |
| R-7 | 80 | — | — | — | 20 | — | — | | 10,500 |
| R-8 | 40 | — | 20 | 35 | — | 5 | — | | 10,700 |
| R-9 | 40 | — | 20 | 35 | — | — | 5 | | 16,940 |
| R-10 | 40 | — | — | 60 | — | — | — | | 10,620 |
| R-11 | 20 | 70 | — | — | 10 | — | — | | 18,600 |

TABLE 2

| Example No. and Comparative Example No. | Matrix Resin No. | Composition [% by weight] | | | | | Filler Filling Rate (% by weight) |
|---|---|---|---|---|---|---|---|
| | | Matrix Resin Including Polymerization Catalyst | Organic-Inorganic Composite Filler | Inorganic Filler A | Inorganic Filler B | Inorganic Filler C | |
| Example 1 | R-1 | 13.0 | 29.9 | 25.7 | 29.9 | 1.5 | 87 |
| Example 2 | R-1 | 13.0 | 25.7 | 25.7 | 34.1 | 1.5 | 87 |
| Example 3 | R-1 | 13.0 | 21.5 | 29.9 | 34.1 | 1.5 | 87 |
| Example 4 | R-1 | 20.0 | 15.6 | 31.1 | 31.1 | 2.2 | 80 |
| Example 5 | R-2 | 20.0 | 15.6 | 31.1 | 31.1 | 2.2 | 80 |
| Example 6 | R-4 | 20.0 | 15.6 | 31.1 | 31.1 | 2.2 | 80 |

TABLE 2-continued

| Example | | | | | | | |
|---|---|---|---|---|---|---|---|
| Example 7 | R-8 | 20.0 | 15.6 | 31.1 | 31.1 | 2.2 | 80 |
| Example 8 | R-9 | 20.0 | 15.6 | 31.1 | 31.1 | 2.2 | 80 |
| Example 9 | R-10 | 20.0 | 15.6 | 31.1 | 31.1 | 2.2 | 80 |
| Comp. Ex. 1 | R-3 | 20.0 | 15.6 | 31.1 | 31.1 | 2.2 | 80 |
| Comp. Ex. 2 | R-1 | 20.0 | 0 | 46.7 | 31.1 | 2.2 | 80 |
| Comp. Ex. 3 | R-1 | 27.0 | 14.0 | 28.0 | 28.0 | 3.0 | 73 |
| Comp. Ex. 4 | R-5 | 20.0 | 15.6 | 31.1 | 31.1 | 2.2 | 80 |
| Comp. Ex. 5 | R-7 | 20.0 | 15.6 | 31.1 | 31.1 | 2.2 | 80 |
| Comp. Ex. 6 | R-6 | 20.0 | 15.6 | 31.1 | 31.1 | 2.2 | 80 |
| Comp. Ex. 7 | R-11 | 20.0 | 15.6 | 31.1 | 31.1 | 2.2 | 80 |

| Example No. and Comparative Example No. | Operability | | Preservation Stability | | Consistency Maintenance Rate [%] | Polymerization Shrinkage Rate [% by vol] |
|---|---|---|---|---|---|---|
| | Stickiness | Packability | Initial Consistency [mm] | Consistency after Storage at 50° C. [mm] | | |
| Example 1 | A | A | 15.0 | 14.1 | 94 | 1.75 |
| Example 2 | A | A | 15.3 | 14.6 | 95 | 1.74 |
| Example 3 | A | A | 15.4 | 14.9 | 97 | 1.76 |
| Example 4 | A | B | 19.4 | 18.6 | 96 | 2.10 |
| Example 5 | A | B | 19.8 | 19.2 | 97 | 2.05 |
| Example 6 | A | B | 19.8 | 18.8 | 95 | 2.07 |
| Example 7 | A | B | 18.8 | 17.5 | 93 | 2.10 |
| Example 8 | A | A | 15.9 | 15.1 | 95 | 2.05 |
| Example 9 | A | A | 16.3 | 15.4 | 94 | 1.98 |
| Comp. Ex. 1 | A | C | 21.2 | 17.6 | 83 | 2.12 |
| Comp. Ex. 2 | B | D | 21.5 | 21.3 | 99 | 2.43 |
| Comp. Ex. 3 | B | D | 24.0 | 23.8 | 99 | 3.03 |
| Comp. Ex. 4 | A | C | 22.5 | 18.5 | 82 | 2.13 |
| Comp. Ex. 5 | A | B | 19.7 | 16.5 | 84 | 2.41 |
| Comp. Ex. 6 | A | C | 23.0 | 18.4 | 80 | 2.23 |
| Comp. Ex. 7 | B | A | 17.2 | 16.3 | 95 | 2.01 |

Examples 1 to 9

All of the dental curing compositions of Examples 1 to 9 had little stickiness and presented excellent packability. Examples 1 to 9 presented excellent preservation stability with the consistency maintenance rate that was equal to or higher than 90%, and presented low polymerization shrinkage rates.

Comparative Examples 1 and 4

The dental curing compositions of Comparative Examples 1 and 4 did not satisfy the requirement of the present invention due to the fact that these dental curing compositions used the matrix resin having viscosity that was lower than 10,000 mPa·s at 25° C. As a result, the dental curing compositions of Comparative Examples 1 and 4 had inferior packability and each presented a consistency maintenance rate that was lower than 85%.

Comparative Example 2

The dental curing composition of Comparative Example 2 did not satisfy the requirement of the present invention due to the fact that this dental curing composition had no organic-inorganic composite filler blended therein. As a result, the dental curing composition of Comparative Example 2 had high stickiness, and inferior packability, and presented a high polymerization shrinkage rate.

Comparative Example 3

As to the dental curing composition of Comparative Example 3, the total content of organic-inorganic composite filler and inorganic filler was lower than 75% by weight. As a result, the dental curing composition of Comparative Example 3 had high stickiness, and inferior packability, and presented a high polymerization shrinkage rate.

Comparative Example 5

The dental curing composition of Comparative Example 5 did not satisfy the requirement of the present invention due to the fact that this dental curing composition used the matrix resin in which the content of the low viscosity polymerizable monomer was larger than 10% by weight. As a result, the dental curing composition of Comparative Example 5 presented a consistency maintenance rate that was lower than 85% and a high polymerization shrinkage rate.

Comparative Example 6

The dental curing composition of Comparative Example 6 did not satisfy the requirement of the present invention due to the fact that this dental curing composition used the matrix resin in which the content of the low viscosity polymerizable monomer was higher than 10% by weight and that the viscosity of another matrix resin at 25° C. was lower than 10,000 mPa·s. As a result, the dental curing composition of Comparative Example 6 had inferior packability, and presented a low consistency maintenance rate that was 80%.

Comparative Example 7

The dental curing composition of Comparative Example 7 did not satisfy the requirement of the present invention due to the fact that this dental curing composition used the matrix resin in which the viscosity at 25° C. was higher than 17,000 mPa·s. As a result, the dental curing composition of Comparative Example 7 had high stickiness.

From the above results, the dental curing composition of the present invention had low stickiness, presented excellent packability, also presented excellent preservation stability, and presented a low polymerization shrinkage rate.

INDUSTRIAL APPLICABILITY

According to the present invention, a dental curing composition is provided to restore a lost portion of a tooth generated due to dental caries, tooth fracturing, etc. More particularly, a dental curing composition is provided that has the paste character suitable for restoring a posterior tooth, that is excellent in the form shaping property, that has the preservation stability for its paste character, and that also has a low polymerization shrinkage property.

The invention claimed is:

1. A dental curing composition comprising:
   (a) a matrix resin having a viscosity at 25° C. of 10,000 to 17,000 mPa·s, and comprising a low viscosity polymerizable monomer having a viscosity at 25° C. equal to or lower than 100 mPa·s, wherein a content of the low viscosity polymerizable monomer is equal to or higher than 0.01% by weight and equal to or lower than 10% by weight relative to 100% by weight of the matrix resin,
   (b) an organic-inorganic composite filler,
   (c) an inorganic filler, and
   (d) a polymeric initiator,
   wherein the content of the matrix resin (a) in the dental curing composition is from 10 to 25% by weight relative to 100% by weight of the dental curing composition, and
   the total content of the organic-inorganic composite filler (b) and the inorganic filler (c) is from 75% to 90% by weight relative to 100% by weight of the dental curing composition.

2. The dental curing composition of claim 1, wherein the content of the organic-inorganic composite filler (b) is 15 to 35% by weight relative to 100% by weight of the dental curing composition.

3. The dental curing composition of claim 1, wherein a consistency maintenance rate of the dental curing composition after storage thereof at 50° C. for one month is equal to or higher than 85%.

* * * * *